US00H002247H

(19) United States
(12) Statutory Invention Registration
Medve

(10) Reg. No.: US H2247 H
(43) Published: Aug. 3, 2010

(54) PORTABLE MEDICAL EQUIPMENT SUITE

(75) Inventor: Robert Frank Medve, Orange Park, FL (US)

(73) Assignee: The United States of America as represented by the Secretary of the Navy, Washington, DC (US)

(21) Appl. No.: 11/481,227

(22) Filed: Jul. 5, 2006

(51) Int. Cl.
*A61N 1/00* (2006.01)
*A61B 19/02* (2006.01)

(52) U.S. Cl. ..... 607/5; 312/209

(58) Field of Classification Search ..... 607/5; 312/209; 220/23.2, 23.88
See application file for complete search history.

(56) References Cited

U.S. PATENT DOCUMENTS 3,428,383 A * 2/1969 Nobel ..... 312/209
4,790,610 A * 12/1988 Welch et al. ..... 312/218
5,117,521 A 6/1992 Foster et al.
5,457,831 A 10/1995 Foster et al.
5,916,096 A 6/1999 Wiesmann et al.
5,964,065 A 10/1999 Migurski et al.
6,360,389 B1 3/2002 Gallant et al.
6,493,890 B2 12/2002 Smeed
6,725,483 B2 4/2004 Gallant et al.
6,842,922 B2 1/2005 Smeed
2003/0227236 A1 * 12/2003 Brooks ..... 312/100

* cited by examiner

*Primary Examiner*—Dan Pihulic
(74) *Attorney, Agent, or Firm*—Mark O. Glut

(57) ABSTRACT

A portable medical equipment suite that includes a case, a power distribution system, a physiological monitoring and defibrillation system, a portable suction unit, a medical information management system and an oxygen dispenser. The case has a door and an interior, the door allows access to the interior of the case; the case is self contained and waterproof when the door is closed. The power distribution system, the physiological monitoring and defibrillation system, the portable suction unit, the medical information management system, and the oxygen dispenser are disposed within the interior of the case. The power distribution system powers the physiological monitoring and defibrillation system, the portable suction unit, and the medical information management system.

18 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PORTABLE MEDICAL EQUIPMENT SUITE

STATEMENT OF GOVERNMENT INTEREST

The invention described herein may be manufactured and used by or for the Government of the United States of America for governmental purposes without payment of any royalties thereon or therefor.

BACKGROUND

The present invention relates to a portable medical equipment suite. More specifically, but without limitation, the present invention relates a portable medical equipment suite that can be deployed on helicopters and can be used on patients known or assumed to be in critical condition and require trauma treatment.

There are many rescue operations and evacuation operations, particularly in military situations, that are made by helicopter. People or military personnel with life threatening injuries that need immediate evacuation from the point of injury are typically evacuated by helicopter.

Studies show that nearly 70 percent of deaths resulting from injuries received in battle occur within the first hour. Battle experts state that the most critical time for treatment of a casualty is the first ten minutes after an injury occurs. Therefore, for optimum survivability an injury should be treated within 10 minutes of occurrence.

Currently the United States military utilizes three different medical equipment suite configurations in military rotary wing aircraft (e.g. helicopters). The first type of suite configuration is the fully integrated suite, such as the U.S. Army's UH-60Q aircraft. This suite configuration is integrated within the aircraft and includes the best possible equipment. The aircraft is very expensive and there are not enough UH-60Q deployed to be effective.

The second type of suite is the partially integrated suite that can be found on the U.S. Army's HH-60L. Some equipment is integrated into the aircraft while other equipment remains separate. In the partially integrated suite, there are problems with the stowage of gear and equipment and the survivability of the suite on the military battlefield.

The third type of medical equipment suite configuration is non-integrated medical equipment, which is equipment taken by medical personnel on board the aircraft. This equipment is usually not properly stowed and/or not adequately protected from potential damage.

Prior solutions that have been used or proposed are generally unsatisfactory. One solution included a stretcher bridge which holds instruments, and straddles a stretcher (the stretcher bridge bridges over the patient on a stretcher). In this solution, the equipment is exposed to the elements, requires an outside or external power supply and is not a fully self contained unit. Another solution includes a single enclosure mounted to the rear wall of an aircraft to provide a flight surgeon with a full range of intensive care equipment. However, this system is not portable and the aircraft needs to be specially equipped with the system.

For the foregoing reasons, there is a need for a portable medical equipment suite that can be transported quickly in and out of different airframes and/or vehicles.

SUMMARY

The present invention is directed to a portable medical equipment suite that meets the needs enumerated above and below.

The present invention is directed to a portable medical equipment suite that includes a case, a power distribution system, a physiological monitoring and defibrillation system, a portable suction unit, a medical information management system and an oxygen dispenser. The case has a door and an interior, the door allows access to the interior of the case; the case is self contained and waterproof when the door is closed. The power distribution system, the physiological monitoring and defibrillation system, the portable suction unit, the medical information management system, and the oxygen dispenser are disposed within the interior of the case. The power distribution system powers the physiological monitoring and defibrillation system, the portable suction unit, and the medical information management system.

It is a feature of the present invention to provide a portable medical equipment suite that is portable and can be moved easily from location to location and can be used or installed in multiple types of venues, aircraft, or vehicles.

It is a feature of the present invention to provide a portable medical equipment suite where medical equipment is disposed within a case such that the medical equipment is not exposed to the elements. It is a further feature of the present invention to provide a portable medical equipment suite that is self-contained.

It is a feature of the present invention to provide a portable medical equipment suite that an operator may utilize already purchased medical equipment.

It is a feature of the present invention to provide a portable medical equipment suite that can support and/or monitor at least one critical trauma patient for treatment or transport.

DRAWINGS

These and other features, aspects and advantages of the present invention will become better understood with reference to the following description and appended claims, and accompanying drawings wherein:

DESCRIPTION

Figure 1:
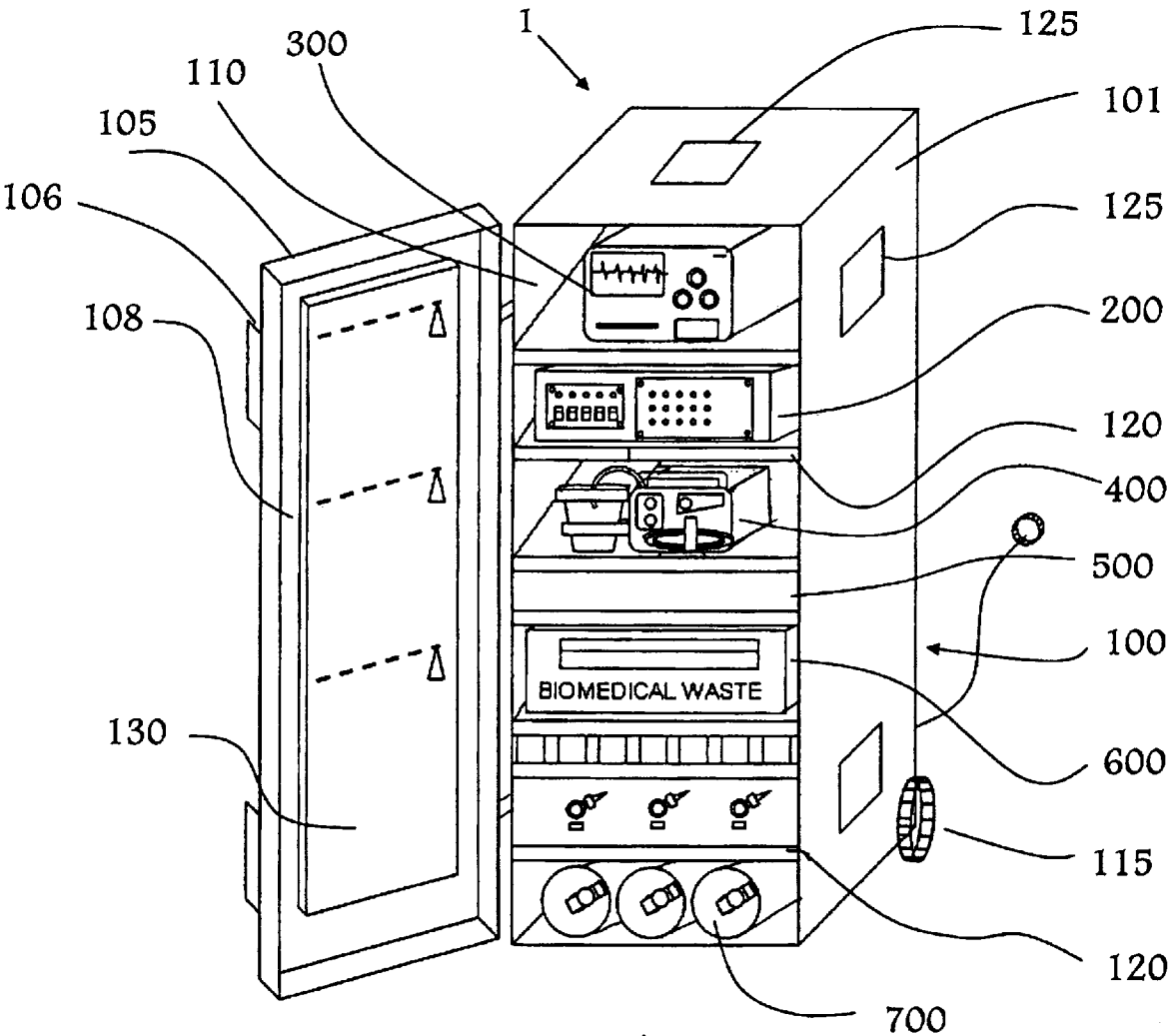
FIG. 1 is a perspective view of an embodiment of the portable medical equipment suite.
Figure 2:
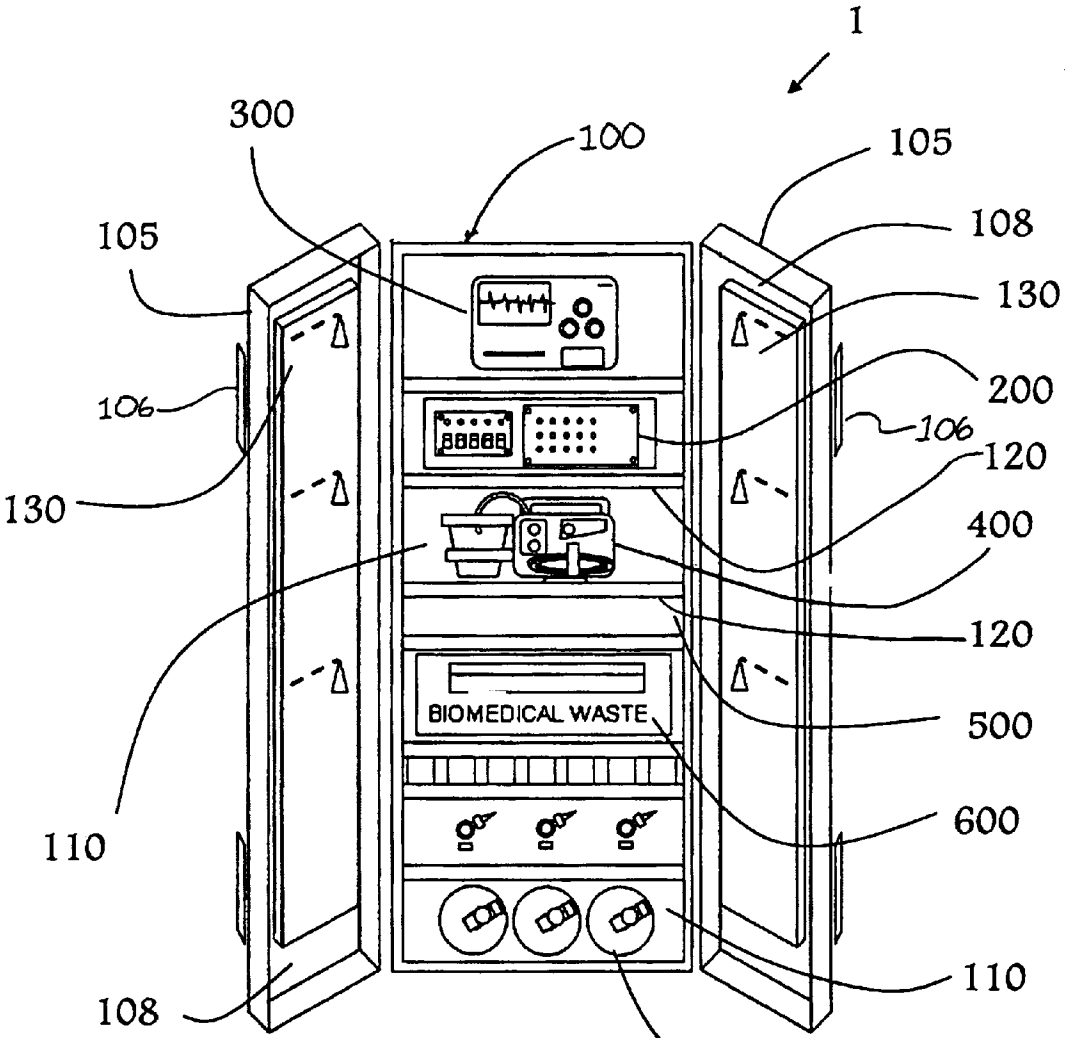
FIG. 2 is a front view of another embodiment of the medical equipment suite.
Figure 3:
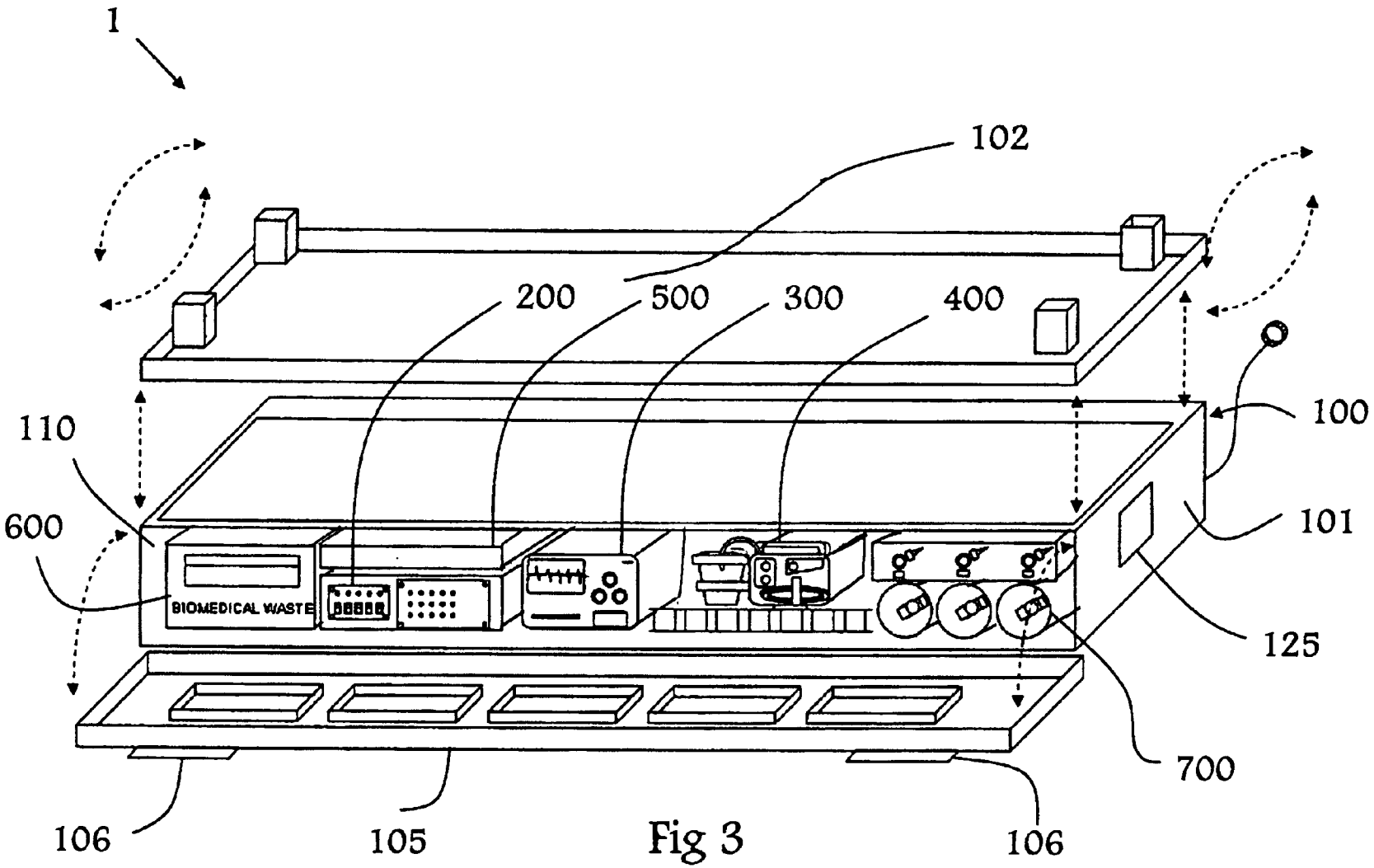
FIG. 3 is an exploded perspective view of another embodiment of the medical equipment suite.

Several embodiments of the present invention are illustrated by way of example in FIGS. 1-4. As shown in FIG. 1, the portable medical equipment suite 1 includes a case 100, a power distribution system 200, a physiological monitoring and defibrillation system 300, a portable suction unit 400, a medical information management system 500, a bio-waste disposal container 600, and an oxygen dispenser 700. The case 100 includes a door 105 and an interior 110, the door 105 allowing access to the interior 110 of the case 100. The door 105 may be hinged (as shown in FIG. 1) and/or removable (as shown in FIG. 3). In the interior 110 of the case 100, the case 100 may include an adjustable rack system 120 and a zippered storage pouch 130 for accessories. In one of the embodiments of the invention, the zippered storage pouch 130 may be disposed on the inside portion 108 of the door 105. The inside portion 108 of the door may be described as the side of the door 105 that faces the interior 110 of 100 of the case when the door 105 is closed. The case 100 may be self contained, and waterproof when the door 105 is closed. The power distribution system 200 is disposed within the interior 110 of the case 100 and powers the physiological monitoring and defibrillation system 300, the portable suction unit 400, and the medical information management system 500 (as well as any additional components that require a power source). The physiological monitoring and defibrillation system 300, the portable suction unit 400, the medical information management system 500, the bio-waste disposal container 600, and the oxygen dispenser 700 may all be disposed within the interior 110 of the case 100.

In the description of the present invention, the invention will be discussed in a military rescue helicopter environment; however, this invention can be utilized for any type of need that requires use of a portable medical equipment suite. The portable medical equipment suite 1 may be used, but without limitations, in disaster preparedness/response operations, fire rescue units and emergency medical operations.

The case 100 may have an outer shell 101 that is water proof, shock proof and/or non-corrosive. The case 100 may be manufactured from rotomolded polyethylene, injection-molded polymer, or any material practicable. As seen in FIG. 2, in one of the embodiments of the invention, the case 100 may include two doors 105. The doors 105 may include retractable door handles 106 to close and open the doors 105. Optionally, as seen in FIG. 1, the case may include lockable casters 115 or wheels and/or rollers so that the suite 1 may be easily moved, and then locked into place. The case 100 may also include grips 125 for moving the suite 1. The grips 125 may be manufactured from zinc, yellow chromate, plastic, a combination thereof, or any material practicable. The case 100 may also include, but without limitation, a lid hanger, an airtight breather valve/humidity indicator, lifting/tie down rings, a lockable cable/hasp, a purge valve and/or a desiccant basket. Also, disposed within the interior 110 of the case 100 there may be additional adjustable rack systems 120 for housing any additional components or medical supplies.

Figure 4:
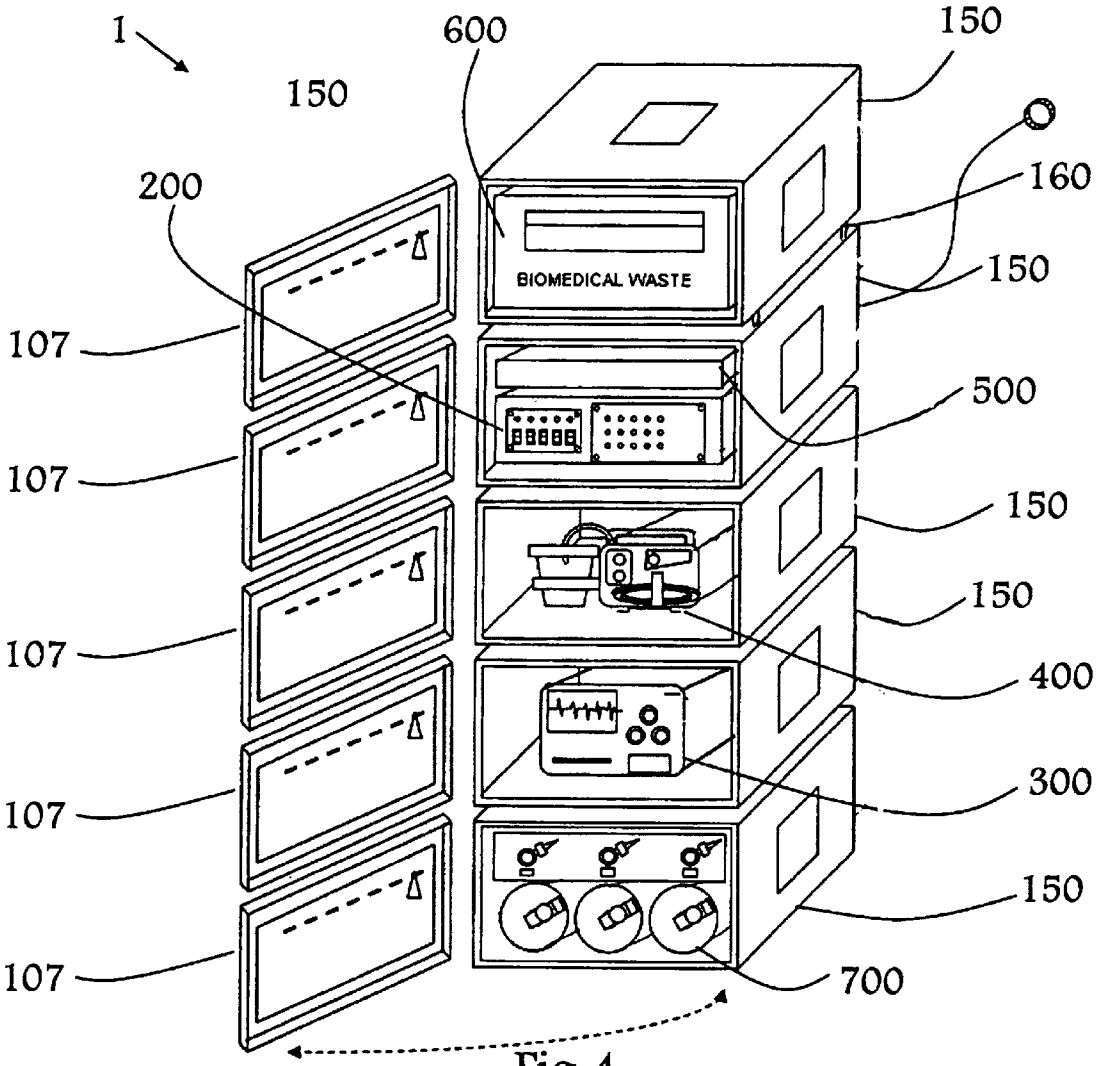
FIG. 4 is an exploded perspective view of the modular embodiment of the medical equipment suite.

The portable medical equipment suite 1, as well as the case 100, may be arranged vertically, as shown in FIGS. 1 and 2, or horizontally as shown in FIG. 3. In the horizontal configuration, the top 102 of the case 100 may function as a gurney. The case 100 may also be modular in nature. As seen in FIG. 4, each specific medical component (the physiological monitoring and defibrillation system 300, the portable suction unit 400, the oxygen dispenser 700, etc.) may be disposed within a separate module 150. Each module 150 may be openable and have a module door 107 to protect the component from the environment and allow access to the individual component. The module doors 107 may be hinged (not shown) or completely removable (as shown in FIG. 4). Each module 150 may be water proof, shock proof and non-corrosive. The modules 150 can be arranged in a vertical, a horizontal fashion or in a combination of both configurations. The modules 150 may be connectable to each other via a module connection system 160 and can be configured to allow electronic communication between the components. The module connection system 160 may be snap system, a male female connection, a quick disconnect system, or any type connection system that attaches the individual modules 150 to each other.

The power distribution system 200 supplies power to all the components of the portable medical equipment suite 1 that require any type of power. The power distribution system 200 may be, but without limitation, a universal power pack, a battery, or any other type of self sustaining power distribution system. The power distribution system 200 may include an outlet power strip (e.g. a 6 or 8 outlet power strip) so that it can power several components at the same time. In addition, the power distribution system 200 may be attachable to an external power supply such as an outlet or the airframe power supply. The power distribution system 200 may be attached and powered by alternating current (AC) or direct current (DC) sources or any type of power practicable.

When introducing elements of the present invention or the preferred embodiment(s) thereof the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to a certain preferred embodiments thereof, other embodiments are possible. Therefore, the spirit and scope of the appended claims should not be limited to the description of the preferred embodiment(s) contained herein.

What is claimed is:

1. A portable medical equipment suite comprising:

a case, the case having a door and an interior, the door allowing access to the interior of the case, the case being self contained and waterproof when the door is closed;

a power distribution system, the power distribution system disposed within the interior of the case;

a physiological monitoring and defibrillation system, the physiological monitoring and defibrillation system disposed within the interior of the case, the physiological monitoring and defibrillation system powered by the power distribution system;

a portable suction unit, the portable suction unit disposed within the interior of the case, the portable suction unit powered by the power distribution system;

a medical information management system, the medical information management system disposed within the interior of the case, the medical information management system powered by the power distribution system, and, an oxygen dispenser, the oxygen dispenser disposed within the interior of the case.

2. The portable medical equipment suite of claim 1, further including a bio-waste disposal container, the bio-waste disposal container disposed within the interior of the case.

3. The portable medical equipment suite of claim 2, wherein the case has an outer shell.

4. The portable medical equipment suite of claim 3, wherein the outer shell is water proof, shock proof and non-corrosive.

5. The portable medical equipment suite of claim 4, wherein the shell is manufactured from a group of materials consisting of rotomolded polyethylene and injection-molded polymer.

6. The portable medical equipment suite of claim 3, wherein the case includes lockable casters for moving the suite from place to place and being able to lock the suite into place.

7. The portable medical equipment suite of claim 6, wherein the case includes grips disposed on the outer shell.

8. The portable medical equipment suite of claim 7, wherein the door has a door handle.

9. The portable medical equipment suite of claim 8, further including an adjustable rack system for holding medical components and supplies, the adjustable rack system disposed within the interior of the case.

10. The portable medical equipment suite of claim 8, further including a zippered storage pouch for holding medical supplies, the pouch disposed on the inside of the door.

11. A portable medical equipment suite comprising:

modules;

a power distribution system, the power distribution system disposed within one of the modules;

a physiological monitoring and defibrillation system, the physiological monitoring system disposed within its own module, the physiological monitoring system powered by the power distribution system;

a portable suction unit, the portable suction unit disposed within its own module, the portable suction unit powered by the power distribution system;

a medical information management system, the medical information management system disposed within its own module, the medical information management system powered by the power distribution system, and, an oxygen dispenser, the oxygen dispenser disposed within its own module.

12. The portable medical equipment suite of claim 11, wherein the suite further includes a module connection system for connecting the modules to each other.

13. The portable medical equipment suite of claim l2, wherein the modules are arranged in a horizontal configuration.

14. The portable medical equipment suite of claim 12, wherein the modules are arranged in a vertical configuration.

15. The portable medical equipment suite of claim 12, wherein the modules are arranged in a combination vertical and horizontal configuration.

16. The portable medical equipment of claim 15, wherein each module is water proof, shock proof and non-corrosive.

17. The portable medical equipment of claim 16, wherein each module includes a door allowing access to the interior of the module.

18. The portable medical equipment of claim 12, wherein the suite further including a bio-waste container, the bio-waste container disposed within its own module.

* * * * *